United States Patent
Jaekel

(10) Patent No.: US 8,440,425 B2
(45) Date of Patent: May 14, 2013

(54) METHOD OF PREPARING A BIOLOGICAL SPECIMEN SLIDE

(75) Inventor: Robert Jaekel, Rolling Meadows, IL (US)

(73) Assignee: Abbott Laboratories, Abbott Park, IL (US)

( * ) Notice: Subject to any disclaimer, the term of this patent is extended or adjusted under 35 U.S.C. 154(b) by 1041 days.

(21) Appl. No.: 12/002,579

(22) Filed: Dec. 18, 2007

(65) Prior Publication Data

US 2009/0155783 A1    Jun. 18, 2009

(51) Int. Cl.
- *C12Q 1/68* (2006.01)
- *G01N 1/30* (2006.01)
- *G01N 33/00* (2006.01)
- *C12N 5/00* (2006.01)
- *C12M 1/00* (2006.01)
- *C07H 21/02* (2006.01)

(52) U.S. Cl.
USPC ........ 435/40.5; 435/6.1; 435/325; 435/283.1; 435/287.2; 536/23.1; 422/68.1

(58) Field of Classification Search ............. 435/6.1, 435/40.5, 283.1, 287.2, 325; 536/23.1; 422/68.1
See application file for complete search history.

(56) References Cited

U.S. PATENT DOCUMENTS

| | | | | |
|---|---|---|---|---|
| 3,929,667 A | * | 12/1975 | Bautis | 252/408.1 |
| RE35,589 E | * | 8/1997 | Fisch | 356/246 |
| 5,807,522 A | * | 9/1998 | Brown et al. | 422/50 |
| 5,948,359 A | * | 9/1999 | Kalra et al. | 422/65 |
| 6,026,174 A | * | 2/2000 | Palcic et al. | 382/133 |
| 6,250,867 B1 | * | 6/2001 | Gwyn et al. | 412/19 |
| 6,296,809 B1 | * | 10/2001 | Richards et al. | 422/64 |
| 2002/0102617 A1 | * | 8/2002 | MacBeath et al. | 435/7.9 |
| 2002/0142354 A1 | * | 10/2002 | Wildsmith et al. | 435/7.2 |
| 2003/0047863 A1 | * | 3/2003 | Lang et al. | 271/103 |
| 2004/0009098 A1 | * | 1/2004 | Torre-Bueno | 422/63 |
| 2006/0239868 A1 | * | 10/2006 | Sage et al. | 422/104 |
| 2007/0048770 A1 | | 3/2007 | Jaekel et al. | |

FOREIGN PATENT DOCUMENTS

EP        0623177 B1        10/1997

OTHER PUBLICATIONS de la Torre. Histochemistry. 1976. 49: 81-93.*
Patel. American Journal of Pathology. 1994. 14(1): 7-14.*
Abcam (retrieved on Apr. 23, 2012 from the internet: <url: http://www.abcam.com/PAP-pen-ab2601.html>).*
Super Pap Pen (retrieved on Sep. 13, 2012 from the Internet Archive: http://web.archive.org/web/20031022133038/http://www.daido-sangyo.co.jp/med_5.htm).*

* cited by examiner

*Primary Examiner* — Robert T Crow
*Assistant Examiner* — Joseph G Dauner
(74) *Attorney, Agent, or Firm* — McDermott Will & Emery LLP

(57) ABSTRACT

A method of preparing a slide of a biological specimen, including the steps of (a) providing a slide containing a biological specimen and a cover slip, (b) placing a liquid non-evaporating sealing compound such as mineral oil at spaced locations around an area on the slide and (c) placing the cover slip over the specimen area whereby the specimen and reagent is between the slide and the cover slip and the sealing compound spreads to define a closed boundary around the specimen in the space between the slide and the cover slip. Testing of the biological specimen may then be performed automatically.

19 Claims, 5 Drawing Sheets

METHOD OF PREPARING A BIOLOGICAL SPECIMEN SLIDE

CROSS REFERENCE TO RELATED APPLICATION(S)

Not applicable.

STATEMENT REGARDING FEDERALLY SPONSORED RESEARCH OR DEVELOPMENT

Not applicable.

REFERENCE TO A MICROFICHE APPENDIX

Not applicable.

TECHNICAL FIELD

The present invention is directed toward testing of biological specimens, and particularly toward preparation of slides of biological specimens for use in automatic systems.

BACKGROUND OF THE INVENTION AND TECHNICAL PROBLEMS POSED BY THE PRIOR ART

Biological specimens are tested for a wide variety of reasons. For example, immunohistochemical (IHC) assays and assay techniques based on in situ hybridization (ISH) and, in particular, fluorescent in situ hybridization (FISH) are commonplace techniques used in medical diagnostics today. Biological samples such as tissue or cell samples from suspected or known diseased patients are analyzed using IHC and ISH/FISH techniques to determine or monitor the patient's status with respect to the disease under investigation. However, both IHC and ISH/FISH methods require the performance of numerous complex and time consuming steps in preparing the tissue and cell samples and then carrying out the actual IHC or hybridization assay. When performed manually, these assay methods are tedious, technically demanding and time consuming. Nevertheless, well-established protocols have been established for manual assays. FISH is also discussed in U.S. Patent Publication No. US 2007/0048770 A1, the full disclosure of which is hereby incorporated by reference.

According to common FISH protocols, glass slides may be pre-treated with protease in order to digest cellular proteins that could interfere with DNA hybridization, with protease treatment consisting of a series of steps followed by ethanol dehydration. Additional sample fixation is also required in most cases.

Hybridization and denaturation steps are typically carried out at elevated temperatures that result in evaporation of assay reagents. To prevent excess evaporation, the sample specimens are typically covered on the slides by cover slips sealed around the edge by rubber cement.

Following hybridization, nonspecifically bound probe is washed off the sample, and then DNA is counter-stained with DAPI. However, to accommodate the post-hybridization wash, the rubber cement is peeled off manually to free the cover slip from the slide. The slides can then be immersed into a wash solution to complete the wash.

With the increased volume of testing, automated systems have been increasingly required, particularly for labor intensive procedures and time consuming protocols. Such systems not only increase reliability through consistent performance of required actions, but also reduce labor costs not only by freeing technicians from having to perform particular steps but also by allowing actions to be taken without requiring intervention by technicians (e.g., with time consuming protocols, actions can take place overnight without requiring that a technician be at the laboratory overnight to perform such actions).

However, while various automated systems have been developed to facilitate the processing of FISH assays, not all procedures required in an assay have heretofore been capable of being performed by those automated systems. For example, specimen slides prepared with rubber glue sealing around the edge of the cover slips are not readily adaptable to use in automated systems where the required process involves removal of the cover slip. The rubber glue prevents the automated systems from being able to reliably grasp and remove the cover slip, both by potentially interfering with the necessary contact of the apparatus with the cover slip and by securing the cover slip so securely to the slide that the automated system is unable to apply a sufficient force to pull the cover slip off.

The present invention is directed toward overcoming one or more of the problems set forth above.

SUMMARY OF THE INVENTION

A method of preparing a slide of a biological specimen is provided, including the steps of (a) providing a slide containing a biological specimen and a cover slip, (b) placing a liquid non-evaporating sealing compound around an area on the slide, and (c) placing the cover slip over the specimen whereby the specimen is between the slide and the cover slip and the sealing compound defines a closed boundary around the specimen in the space between the slide and the cover slip.

In one form, the sealing compound is mineral oil.

In a further form, the sealing compound is placed in spaced locations around the area on the slide, and the step of placing the cover slip over the specimen causes the sealing compound to spread to connect the spaced locations and define the closed boundary.

In another form, the slide includes a flat surface with a first raised portion around the area on the slide and a second raised portion around the first raised portion wherein the closed boundary is defined between the first and second raised portions.

In another aspect, a method of performing a FISH assay is provided, including the steps of (a) preparing a biological specimen on a slide, and (b) performing the process on the specimen on an apparatus. The step of preparing a biological specimen on a slide includes (i) placing the biological specimen in the area on the slide, (ii) placing a liquid non-evaporating sealing compound around an area on the slide, and (iii) placing the cover slip over the specimen whereby the specimen is between the slide and the cover slip and the sealing compound defines a closed boundary around the specimen in the space between the slide and the cover slip. The apparatus may include a movable suction member adapted to secure to the cover slip whereby the suction member is moved away from the slide to pull the cover slip off the specimen and sealing compound when access to the specimen is required in the process. The method may also include locating the slide on the apparatus to carry out the FISH process on the specimen.

In one form, the sealing compound is mineral oil.

In another form, the sealing compound is placed as spaced droplets around the area on the slide, and the step of placing the cover slip over the specimen causes the sealing compound to expand to connect the spaced locations and define the closed boundary.

In still another form, the slide includes a flat surface with a first raised portion around the area on the slide and a second raised portion around the first raised portion wherein the closed boundary is defined between the first and second raised portions. In a further form, the sealing compound placing step locates spaced droplets of the sealing compound around the slide first raised portion and inside the slide second raised portion.

In yet another form, the specimen preparing step includes (a) mounting the slide to the apparatus, (b) performing the specimen placing step and the sealing compound placing step, and (c) performing the cover slip placing step by securing the suction member to the cover slip and automatically moving the suction member wherein the suction member releases the cover slip after locating the cover slip over the specimen.

DETAILED DESCRIPTION OF THE INVENTION

In accordance with the present invention, slides of biological specimens are prepared, wherein the slides are readily usable in automated systems in which high temperature processing is accomplished (e.g., hybridization) while preventing undesirable evaporation. The methods of the invention are readily available for any biological assay, such as ISH/FISH and IHC assays where it is desirable to apply a cover slip to a sample slide by automation.

Figure 1:
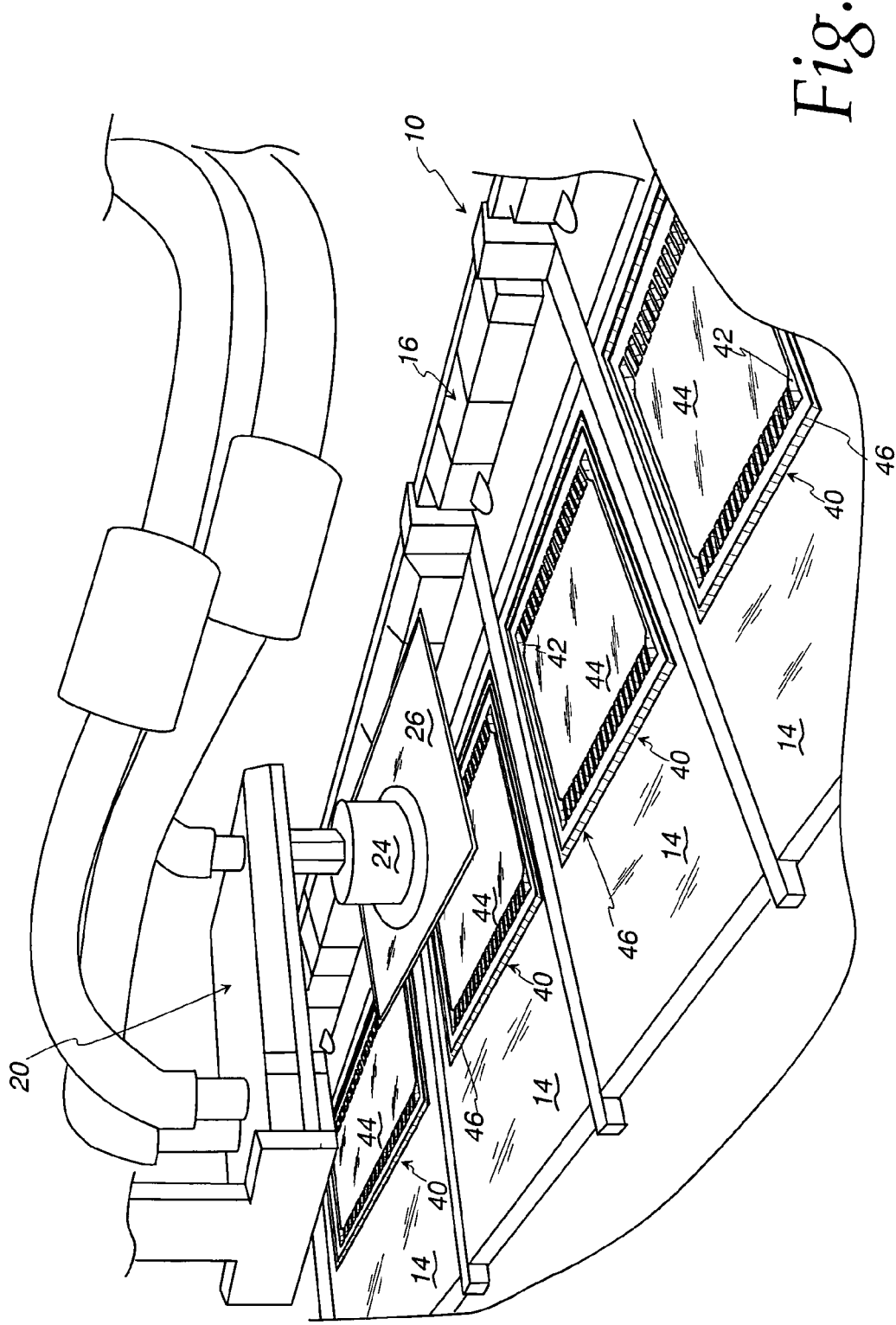
FIG. 1 is a perspective view of a portion of an apparatus of an automated system with which specimen slides prepared according to the present invention may be advantageously used.

FIG. 1 illustrates a portion of an apparatus 10 wherein a plurality of slides 14 are present on a bed or suitable conveyor 16 such as may be used in the system to automatically transport the slides 14 to different locations for the performance of different actions of a testing procedure. It should be appreciated, however, that transportation of the slides 14, if and when required, may be accomplished in any suitable manner in accordance with the present invention.

As shown in FIG. 1, the apparatus 10 includes a controlled head 20 which includes a suitable grasping element (e.g., a suction member 24 such as a suction cup) which may be controlled to both suitably attach to a cover slip 26 whereby the cover slip 26 may be moved onto the slide 14 and released for application onto the slide 14, or may be suitably attached to a cover slip 26 on the slide 14 (e.g., by lowering the suction member 24 to the cover slip 26 and then drawing a suction in the suction member 24) and raised up to remove the cover slip 26 from the slide 14.

Figure 2:
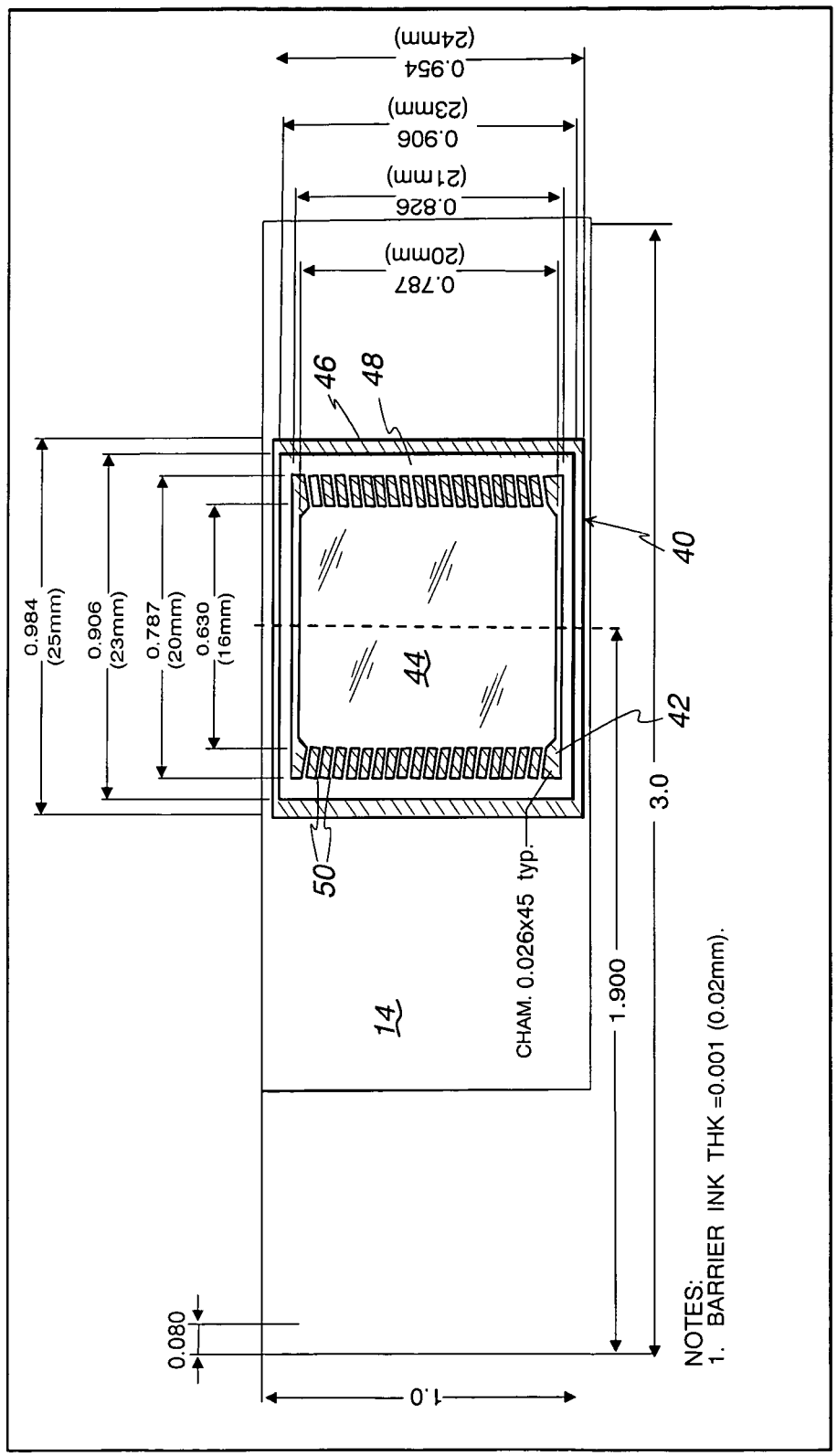
FIGS. 2 and 3 are plan views of various barrier slides usable in the slide preparation method of the present invention.
Figure 3:
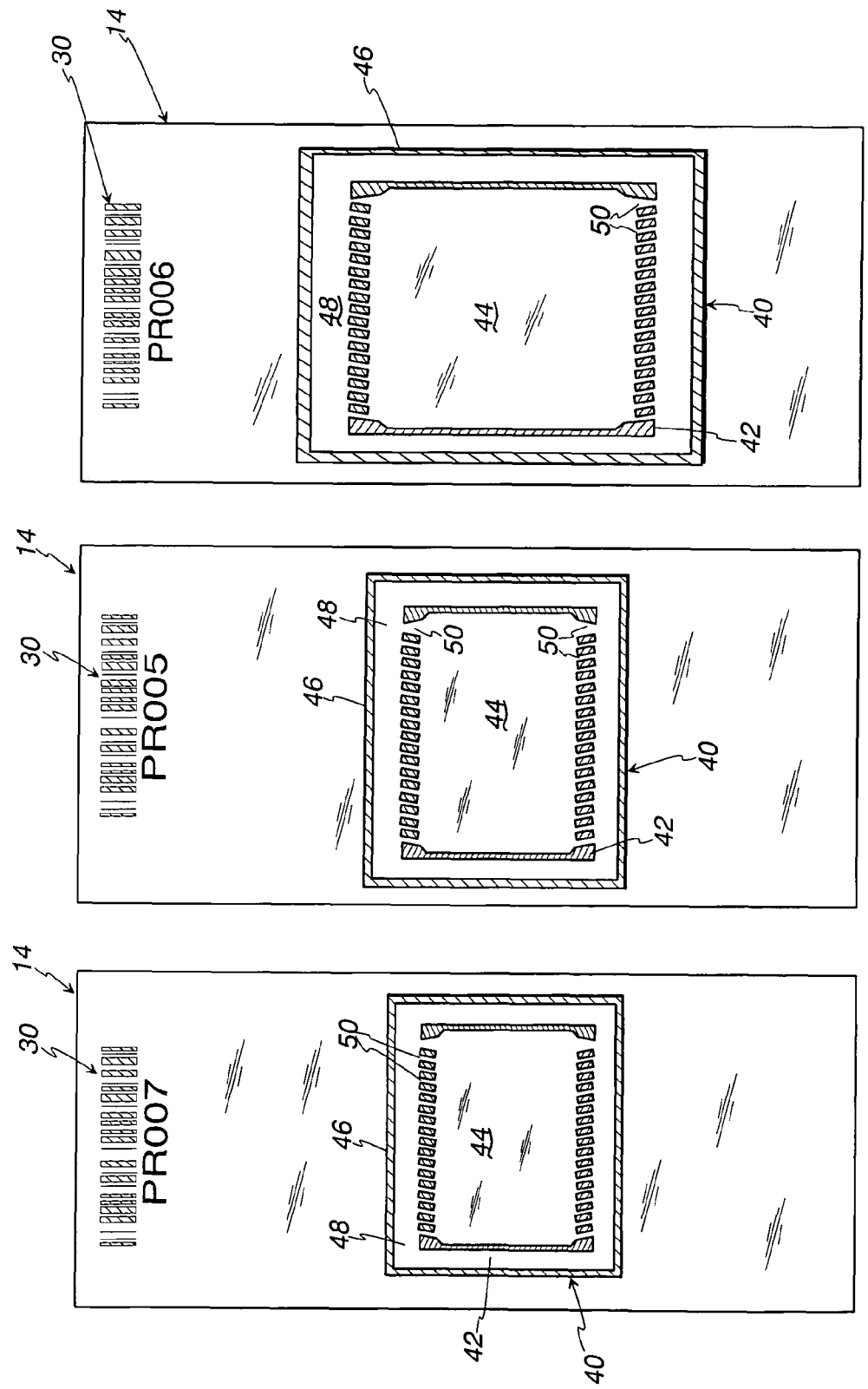

As illustrated in FIG. 1 and further illustrated in FIGS. 2-3, the slides 14 may be made of a suitable material such as glass, and include suitable identifying indicia 30. Further, though not required in all aspects of the present invention, a hydrophobic barrier 40 may also be provided on the slides 14 to contain reagents within the sample test area. Such barrier 40 may be painted on the slides 14, or suitably provided in some other manner such as by etching, so as to provide a raised inner portion 42 around the area 44 on the slide 14 where the specimen is to be placed and a raised outer portion 46 around the inner portion 42. A channel 48 is therefore defined between the inner and outer portions 42, 46. Gaps 50 may also be advantageously provided in the raised inner portion 42 such as may allow gas or other material to pass therethrough if necessary once the specimen and cover slip 26 are located on the slide 14.

In accordance with the present invention, the sample slide is prepared as illustrated in FIGS. 4-7. For example, specimens to be tested by FISH may be cellular (e.g., urine and amniotic fluid) or tissue (e.g., solid tumors). The hydrophobic barrier is advantageously chosen for compatibility with the type of sample and corresponding reagents used in the assay. For example, TEFLON can be used for solid tumors while epoxy can be used for urine based assays that use Carnoy's fixative in processing the sample. The samples may first be advantageously prepared on glass slides 14 having a hydrophobic painted barrier 40. Thereafter, reagents may be added within the area framed by the barrier 40.

Typically a drop 70 with the biological specimen to be tested may advantageously be placed on the slide 14 in the specimen area 44 prior to the drops of sealing compound 60 being placed on the slide 14. Alternatively, it should be understood that it would be within the scope of the present invention for the specimen drop 70 to be added after the drops of sealing compound 60 are added.

Thereafter, drops of sealing compound 60 are placed on the slide 14 around the specimen area 44 (i.e., in the channel 48 if the slide includes a barrier 40 as illustrated). More specifically, the sealing compound 60 can be a liquid non-evaporating sealing compound such as mineral oil. Additional non-evaporating sealing compounds include vegetable and petrochemical based oils and the like.

Figure 4:
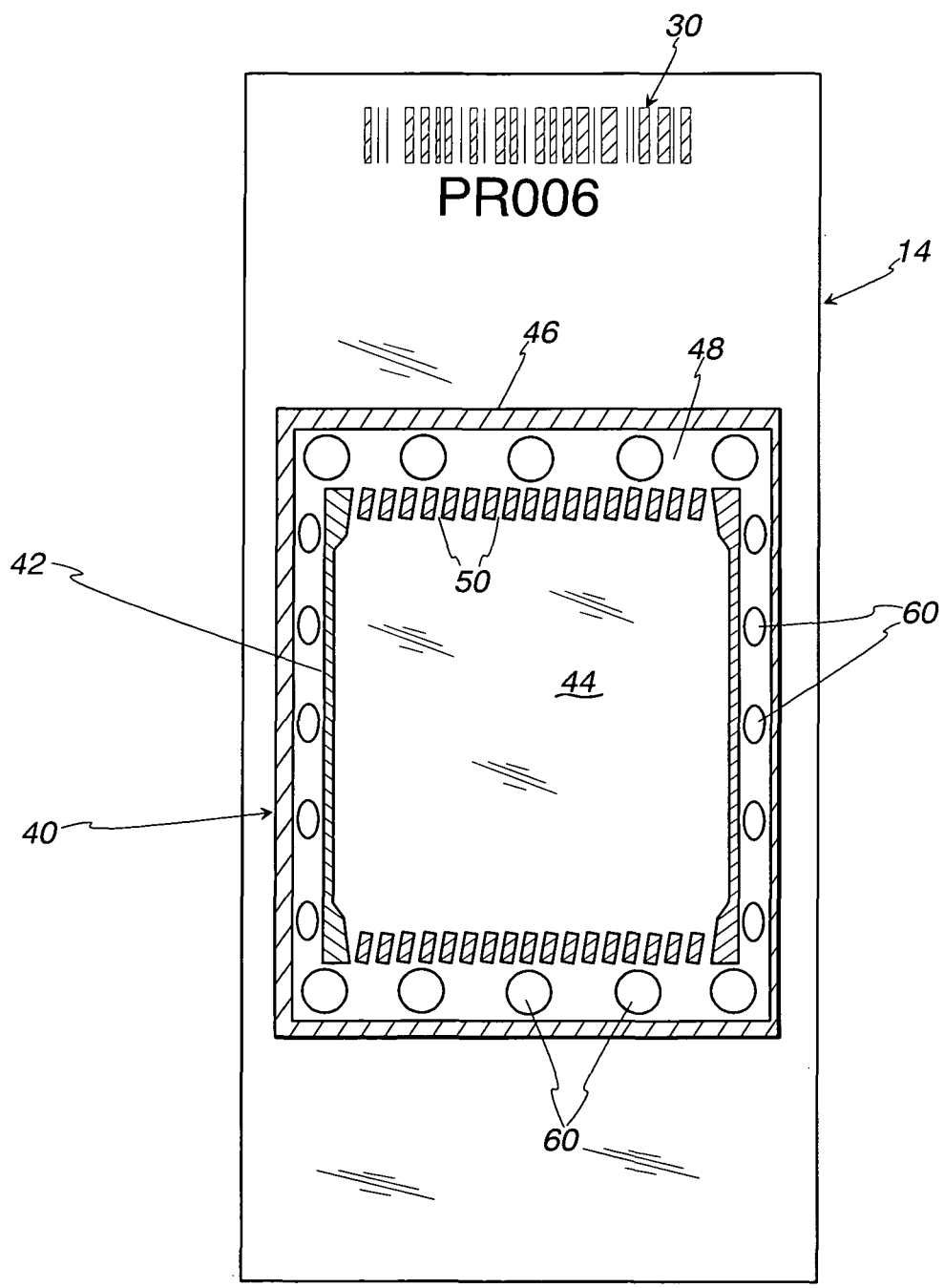
FIG. 4 is a plan view of a barrier slide in which the sealing compound has been first applied according to the method of the present invention.
Figure 5:
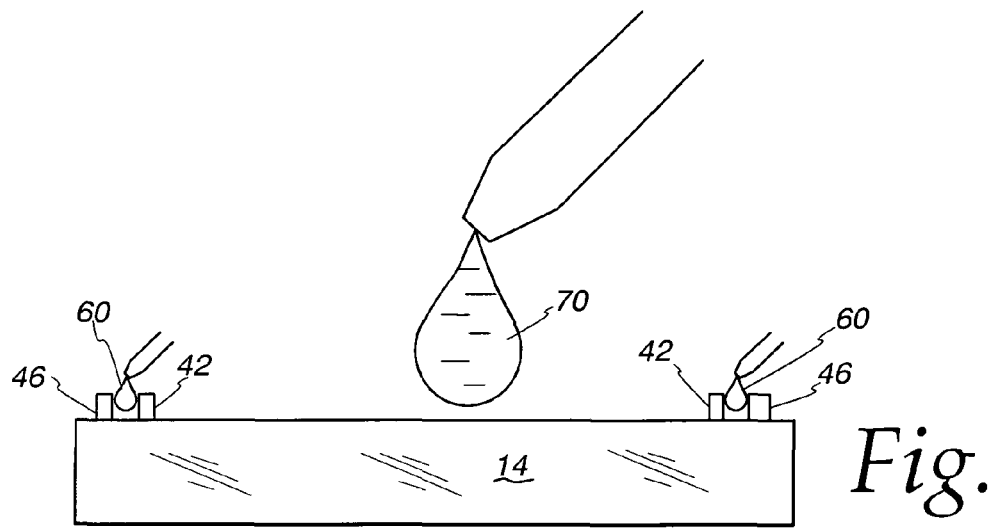
FIG. 5 is a side cross-sectional view illustrating the application of the sealing compound and the biological specimen to the barrier slide according to the present invention.

As best seen in FIG. 4, the drops of sealing compound 60 may be spaced around the area 44, with it being most advantageous that the drops be sufficient in volume and nature so that they will spread out to touch each other and thereby form a closed boundary around the specimen area 44.

Figure 6:
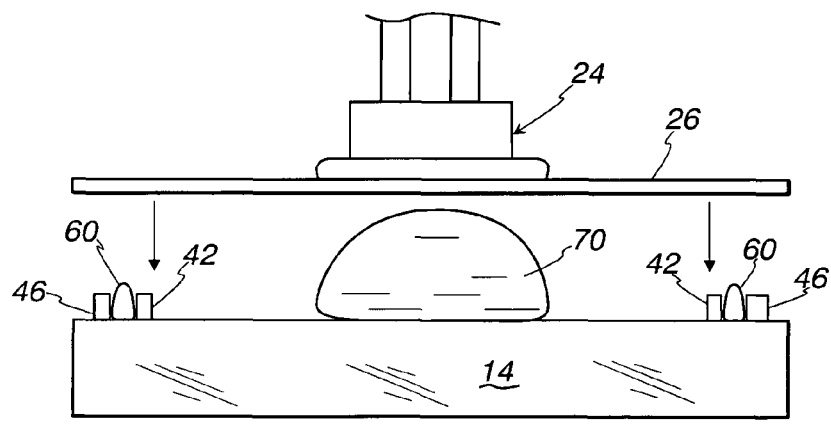
FIG. 6 is a side cross-sectional view illustrating the automated application of a cover slip to a barrier slide prepared according to FIG. 5.
Figure 7:
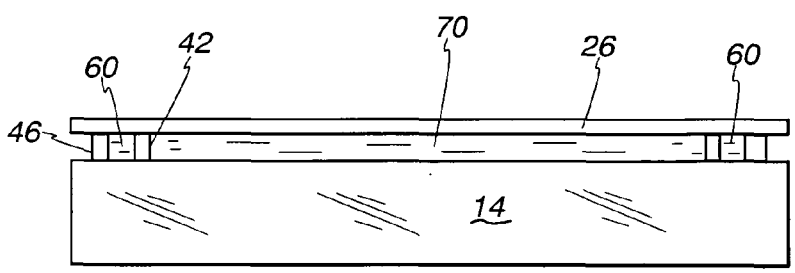
FIG. 7 is a side cross-sectional view illustrating a cover slip applied to a barrier slide with sealing compound and a biological specimen according to the present invention.

With both the sealing compound 60 and the specimen drop 70 on the slide 14, the cover slip 26 may then be lowered onto the slide as illustrated in FIG. 6, and in the process will cause the drops 60, 70 to spread out, including in particularly facilitating the spreading of the sealing compound 60 within the channel 48 all the way around the specimen area 44, to a condition such as shown in FIG. 7. Advantageously, the cover slip can be applied at an angle to provide a more complete seal. It should be appreciated that the compound 60 and specimen 70 will seal with the underside of the cover slip 26 through surface tension therebetween, whereby the entire assembly of slide 14 and cover slip 26 will be held together by the surface tension with the liquids 60, 70 therebetween.

Thereafter, the prepared slide 14 may be used in an automated system such as partially illustrated in FIG. 1. Testing steps which require high temperatures, such as DNA hybridization, or even procedures which require long periods of time, during which evaporation could occur, can thereafter be reliably carried out in the automated system without concern that unacceptable oxidation or evaporation from the specimen area might occur, as the closed boundary defined by the sealing compound 60 will block materials from leaving the specimen area 44 through the space between the slide 14 and cover slip 26.

Moreover, during procedures in which it is necessary to remove the cover slip 26, the suction member 24 of the apparatus 10 may reliably grasp the top of the cover slip 26 (e.g., via suction) and be retracted up to remove the cover slip 26. Since the cover slip 26 is secured solely by the surface tension with the sealing compound 60 and the specimen drop 70, the problem such as would occur with such apparatuses 10 with cover slips secured by rubber glue may be avoided. The surface tension, though sufficiently strong to retain the cover slip 26, is not so strong as to hinder the reliability of the apparatus in grasping and removing the cover slip 26 when necessary. Additionally, heat may be applied to facilitate removal of the cover slip.

It should be appreciated that though the present invention may be advantageously used in conjunction with fully automated systems, the method of the preparing slides of biological specimens itself may also be advantageously carried out manually. Of course, even if the slides 14 are prepared manually, significant labor may be saved in carrying out the testing due to the fact that the slides 14, whether manually or automatically prepared, may be then used in automated systems with minimized or altogether eliminated technician intervention required. Thus, testing procedures may be reliably carried out automatically in the system (e.g., performing FISH on the specimen on the slide 14), even where removal of the cover slip 26 is necessary, including allowing time consuming procedures to be accomplished overnight without the presence of technicians, all also accomplished without unacceptable oxidation or evaporation from the specimen area 44.

Still other aspects, objects, and advantages of the present invention can be obtained from a study of the specification, the drawings, and the appended claims. It should be understood, however, that the present invention could be used in alternate forms where less than all of the objects and advantages of the present invention and preferred embodiment as described above would be obtained.

The invention claimed is:

1. A method of preparing a slide of a biological specimen, comprising the steps of:
   providing a slide and a cover slip;
   placing a biological specimen on the slide in a specimen area;
   placing a liquid non-evaporating sealing compound on said slide around the specimen area; and
   placing the cover slip over the biological specimen and the sealing compound to seal the biological specimen and the sealing compound with the cover slip whereby biological specimen is between said slide and said cover slip and said sealing compound defines a closed boundary around the biological specimen in the space between said slide and said cover slip,
   wherein said slide includes a flat surface with a first raised portion around said specimen area on said slide and a second raised portion around said first raised portion and wherein said closed boundary is defined between said first and second raised portions.

2. The method of claim 1, wherein said sealing compound is mineral oil.

3. The method of claim 1, wherein said sealing compound is placed in spaced locations around said specimen area on said slide, and said step of placing said cover slip over said biological specimen causes said sealing compound to spread to connect said spaced locations and define said closed boundary.

4. The method of claim 1, wherein the sealing compound placing step is performed before the biological specimen placing step.

5. The method of claim 1, wherein the sealing compound placing step is performed after the biological specimen placing step.

6. A method of performing a fluorescence in situ hybridization (FISH) process, comprising the steps of:
   preparing a biological specimen on a slide by:
      placing a biological specimen on the slide in a specimen area;
      placing a liquid non-evaporating sealing compound on said slide around the specimen area,
      placing the cover slip over the biological specimen and the sealing compound to seal the biological specimen and the sealing compound with the cover slip whereby said biological specimen is between said slide and said cover slip and said sealing compound defines a closed boundary around the biological specimen in the space between said slide and said cover slip, wherein said slide includes a flat surface with a first raised portion around said specimen area on said slide and a second raised portion around said first raised portion and wherein said closed boundary is defined between said first and second raised portions; and
   performing said FISH process on said biological specimen on an apparatus.

7. The method of claim 6, wherein said apparatus includes a movable suction member adapted to secure to said cover slip whereby said suction member is moved away from said slide to pull said cover slip off said biological specimen and sealing compound when access to said biological specimen is required in said FISH process.

8. The method of claim 6, wherein said sealing compound is mineral oil.

9. The method of claim 6, wherein said sealing compound is placed as spaced droplets around said specimen area on said slide, and said step of placing said cover slip over said biological specimen causes said sealing compound to expand to connect said spaced locations and define said closed boundary.

10. The method of claim 6, wherein said sealing compound placing step locates spaced droplets of said sealing compound around said first raised portion and inside said second raised portion.

11. The method of claim 6, wherein said specimen preparing step comprises:
   mounting said slide to said apparatus;
   performing said biological specimen placing step and the sealing compound placing step; and
   performing said cover slip placing step by securing a suction member to said cover slip and automatically moving said suction member wherein said suction member releases said cover slip after locating said cover slip over said biological specimen.

12. A method of preparing a slide of a biological specimen, comprising the steps of:
   providing a slide and a cover slip, the slide having a specimen area for receiving a biological specimen and a hydrophobic barrier around the specimen area;
   placing a biological specimen on the slide in the specimen area, the biological specimen contained in the specimen area by the hydrophobic barrier;

placing a liquid non-evaporating sealing compound on the slide around the specimen area; and placing the cover slip over the biological specimen and the sealing compound to seal the biological specimen and the sealing compound with the cover slip whereby the biological specimen is between the slide and the cover slip and the sealing compound defines a closed boundary around the biological specimen in the space between the slide and the cover slip, wherein the slide includes a flat surface with a first raised portion around the specimen area on the slide and a second raised portion around the first raised portion and wherein the closed boundary is defined between the first and second raised portions.

13. The method of claim 12, wherein said sealing compound is mineral oil.

14. The method of claim 12, wherein the sealing compound is placed in spaced locations around the specimen area on the slide, and the step of placing the cover slip over the biological specimen causes the sealing compound to spread to connect the spaced locations and define the closed boundary.

15. The method of claim 12, wherein the sealing compound placing step locates spaced droplets of the sealing compound around the first raised portion and inside the second raised portion.

16. A method of preparing a slide of a biological specimen, comprising the steps of:

providing a slide and a cover slip, the slide having a specimen area for receiving a biological specimen and a hydrophobic barrier around the specimen area;

placing a biological specimen on the slide in the specimen area, the biological specimen contained in the specimen area by the hydrophobic barrier;

placing a liquid non-evaporating sealing compound on the slide around the specimen area; and placing the cover slip over the biological specimen and the sealing compound to seal the biological specimen and the sealing compound with the cover slip whereby the biological specimen is between the slide and the cover slip and the sealing compound defines a closed boundary around the biological specimen in the space between the slide and the cover slip, wherein the hydrophobic barrier comprises a first raised portion around the specimen area and a second raised portion around the first raised portion and wherein the closed boundary is defined between the first and second raised portions.

17. The method of claim 16, wherein the sealing compound placing step locates spaced droplets of the sealing compound around the first raised portion and inside the second raised portion.

18. The method of claim 16, wherein said sealing compound is mineral oil.

19. The method of claim 16, wherein the sealing compound is placed in spaced locations around the specimen area on the slide, and the step of placing the cover slip over the biological specimen causes the sealing compound to spread to connect the spaced locations and define the closed boundary.

* * * * *